US010912451B2

(12) United States Patent
Kobayashi

(10) Patent No.: US 10,912,451 B2
(45) Date of Patent: Feb. 9, 2021

(54) MEDICAL IMAGING APPARATUS, IMAGING METHOD, AND IMAGING APPARATUS

(71) Applicant: SONY CORPORATION, Tokyo (JP)

(72) Inventor: Seiji Kobayashi, Tokyo (JP)

(73) Assignee: Sony Corporation, Tokyo (JP)

( * ) Notice: Subject to any disclaimer, the term of this patent is extended or adjusted under 35 U.S.C. 154(b) by 459 days.

(21) Appl. No.: 15/568,102

(22) PCT Filed: Apr. 5, 2016

(86) PCT No.: PCT/JP2016/001904
§ 371 (c)(1),
(2) Date: Oct. 20, 2017

(87) PCT Pub. No.: WO2016/181602
PCT Pub. Date: Nov. 17, 2016

(65) Prior Publication Data
US 2018/0146846 A1    May 31, 2018

(30) Foreign Application Priority Data
May 12, 2015   (JP) .................. 2015-097020

(51) Int. Cl.
A61B 1/05   (2006.01)
H04N 9/04   (2006.01)
(Continued)

(52) U.S. Cl.
CPC .............. A61B 1/05 (2013.01); A61B 1/04 (2013.01); A61B 5/0077 (2013.01);
(Continued)

(58) Field of Classification Search
CPC combination set(s) only.
See application file for complete search history.

(56) References Cited

U.S. PATENT DOCUMENTS 5,187,572 A    2/1993  Nakamura et al.
7,554,587 B2 *  6/2009  Shizukuishi ....... H04N 9/04561
                                                     348/272
(Continued)

FOREIGN PATENT DOCUMENTS

DE    4136034 A1    5/1992
JP    H0584218 A    4/1993
(Continued)

OTHER PUBLICATIONS

Office Action for JP Patent Application No. 2015-097020, dated Dec. 11, 2018, 5 pages of Office Action and 3 pages of English Translation.
(Continued)

Primary Examiner — Anh Tuan T Nguyen
Assistant Examiner — Shankar Raj Ghimire
(74) Attorney, Agent, or Firm — Chip Law Group

(57) ABSTRACT

There is provided a medical imaging apparatus including a solid-state image sensor that includes a photoelectric converter having at least two photoelectric conversion layers stacked with respect to a light-receiving surface and separating received light into light of different wavelength bands and circuitry configured to control a light source device that illuminates a subject.

7 Claims, 10 Drawing Sheets

(51) Int. Cl.
*A61B 1/04* (2006.01)
*A61B 5/00* (2006.01)
*H01L 27/30* (2006.01)
*H04N 5/225* (2006.01)

(52) U.S. Cl.
CPC .......... *H01L 27/307* (2013.01); *H04N 9/045* (2013.01); *H04N 9/04515* (2018.08); *H04N 2005/2255* (2013.01)

(56) References Cited

U.S. PATENT DOCUMENTS

| | | | | |
|---|---|---|---|---|
| 9,769,430 | B1* | 9/2017 | Bechtel | H04N 7/183 |
| 2006/0181629 | A1 | 8/2006 | Miyashita et al. | |
| 2009/0023991 | A1* | 1/2009 | Gono | A61B 1/00009 |
| | | | | 600/109 |
| 2009/0066787 | A1* | 3/2009 | Yamazaki | A61B 1/0638 |
| | | | | 348/70 |
| 2009/0076322 | A1 | 3/2009 | Matsunaga et al. | |
| 2009/0181339 | A1* | 7/2009 | Liang | A61B 1/0638 |
| | | | | 433/29 |
| 2010/0123070 | A1* | 5/2010 | Natori | H01L 27/14647 |
| | | | | 250/226 |
| 2011/0063427 | A1* | 3/2011 | Fengler | A61B 1/00186 |
| | | | | 348/65 |
| 2011/0122302 | A1* | 5/2011 | Fukunaga | H01L 27/14621 |
| | | | | 348/273 |
| 2011/0260059 | A1* | 10/2011 | Jiang | H01L 27/1461 |
| | | | | 250/330 |
| 2012/0229665 | A1* | 9/2012 | Sharman | H04N 9/045 |
| | | | | 348/222.1 |
| 2013/0062512 | A1* | 3/2013 | Hu | H01L 27/14601 |
| | | | | 250/226 |
| 2015/0094530 | A1* | 4/2015 | Moriya | A61B 1/00009 |
| | | | | 600/103 |
| 2015/0244958 | A1* | 8/2015 | Ohguro | H04N 5/374 |
| | | | | 348/277 |
| 2015/0244995 | A1* | 8/2015 | Sekiguchi | H04N 5/243 |
| | | | | 348/164 |
| 2017/0103497 | A1* | 4/2017 | Cao | G06T 5/003 |
| 2017/0243325 | A1* | 8/2017 | Sasaki | A61B 1/04 |
| 2018/0049633 | A1* | 2/2018 | Fukunaga | H04N 5/3696 |
| 2019/0068922 | A1* | 2/2019 | Miller | H04N 7/0127 |

FOREIGN PATENT DOCUMENTS

| | | |
|---|---|---|
| JP | 3164609 B2 | 5/2001 |
| JP | 2006-228938 A | 8/2006 |
| JP | 2009-528542 A | 8/2009 |
| JP | 2010-201051 A | 9/2010 |
| JP | 2011-142272 A | 7/2011 |
| JP | 2012-213551 A | 11/2012 |
| JP | 2013-034901 A | 2/2013 |
| JP | 2014-113416 A | 6/2014 |
| WO | WO-2016129062 A1 * | 8/2016 .......... A61B 1/00009 |

OTHER PUBLICATIONS

Office Action for JP Patent Application No. 2015-097020, dated Feb. 26, 2019, 6 pages of Office Action and 5 pages of English Translation.

International Search Report and Written Opinion of PCT Application No. PCT/JP2016/001904, dated Jun. 28, 2016, 10 pages of ISRWO.

\* cited by examiner

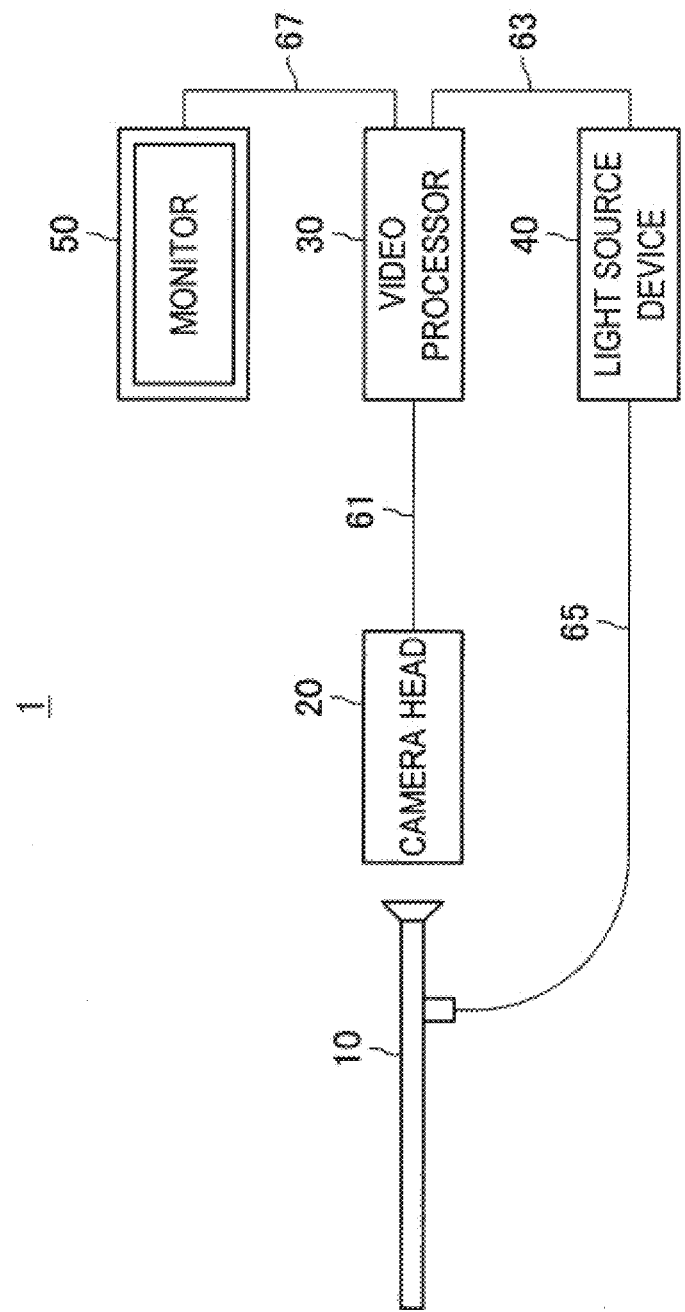
[Fig. 1]

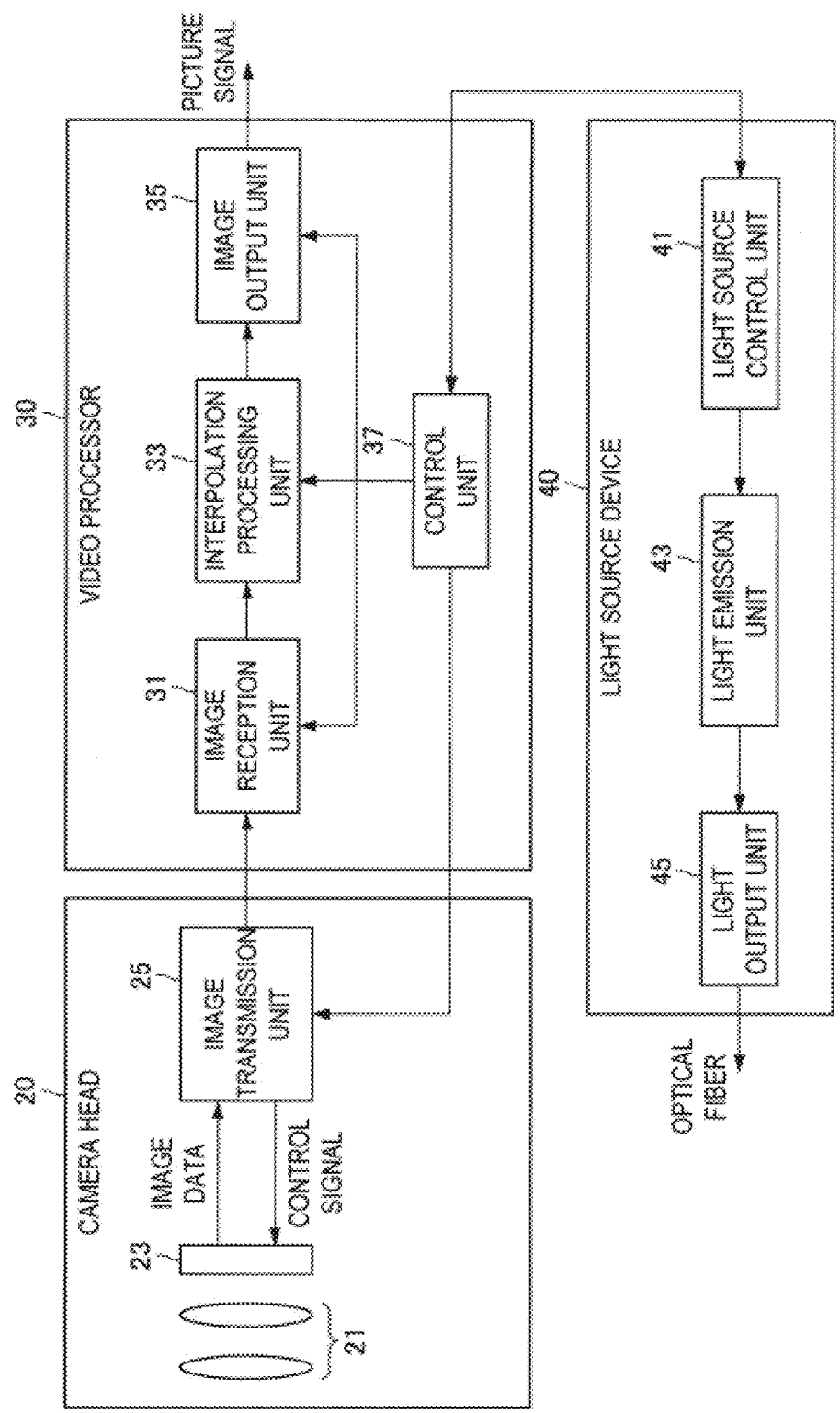
[Fig. 2]

[Fig. 3]
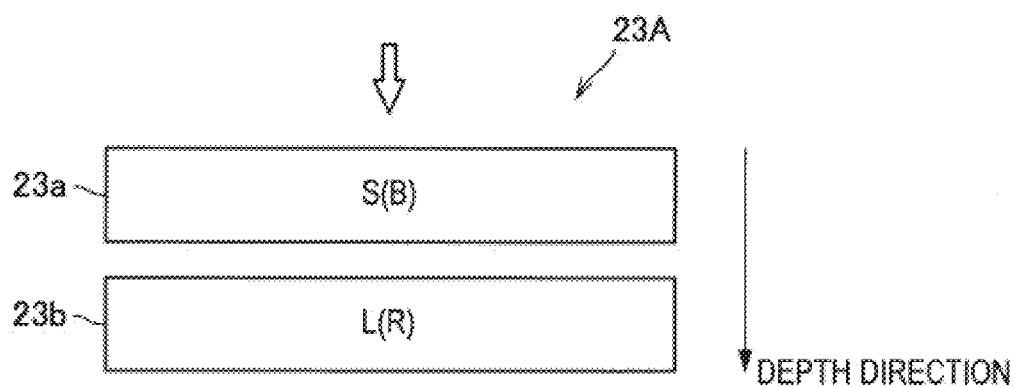
[Fig. 4]
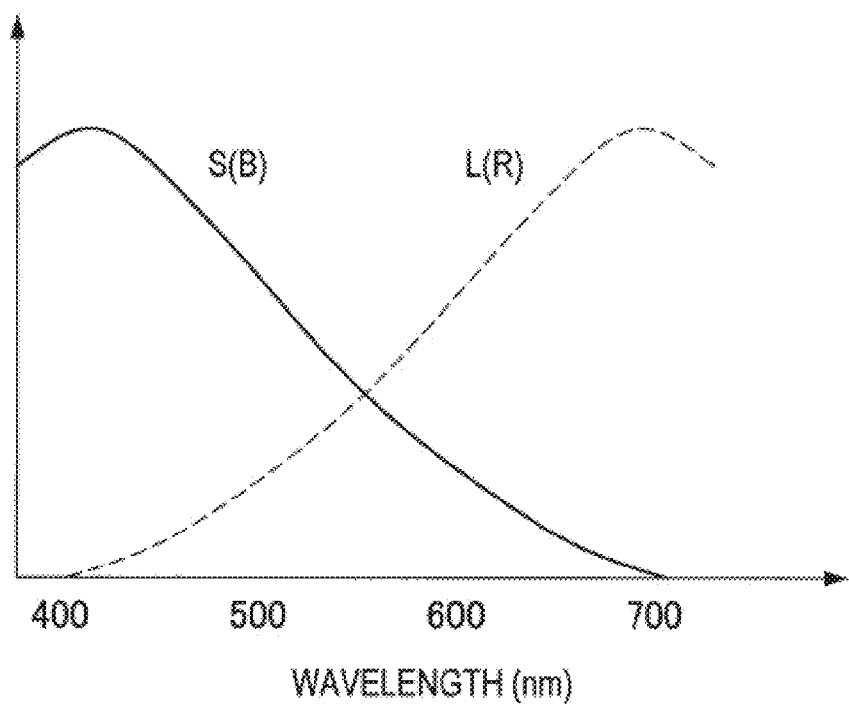

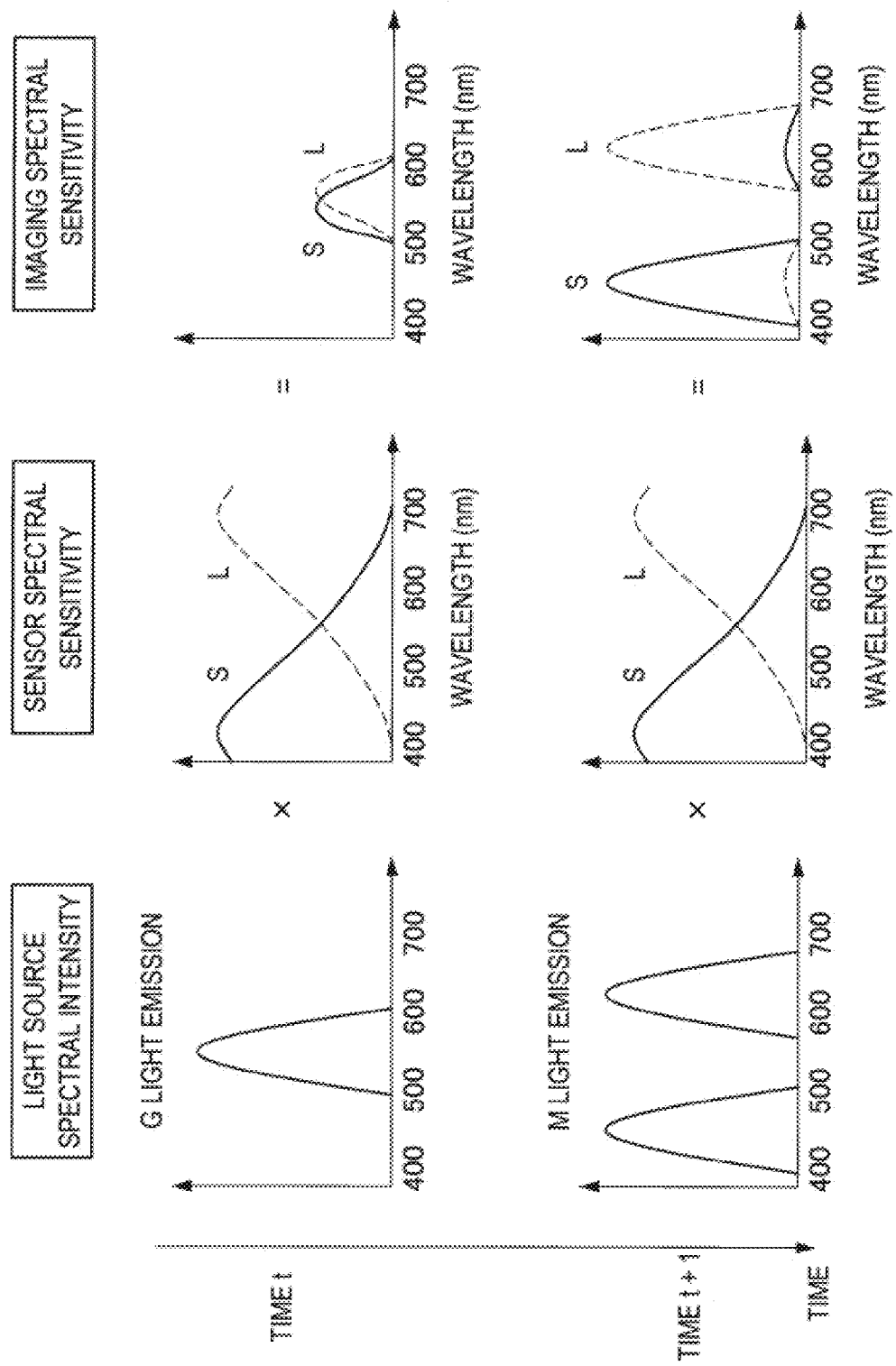
[Fig. 5]

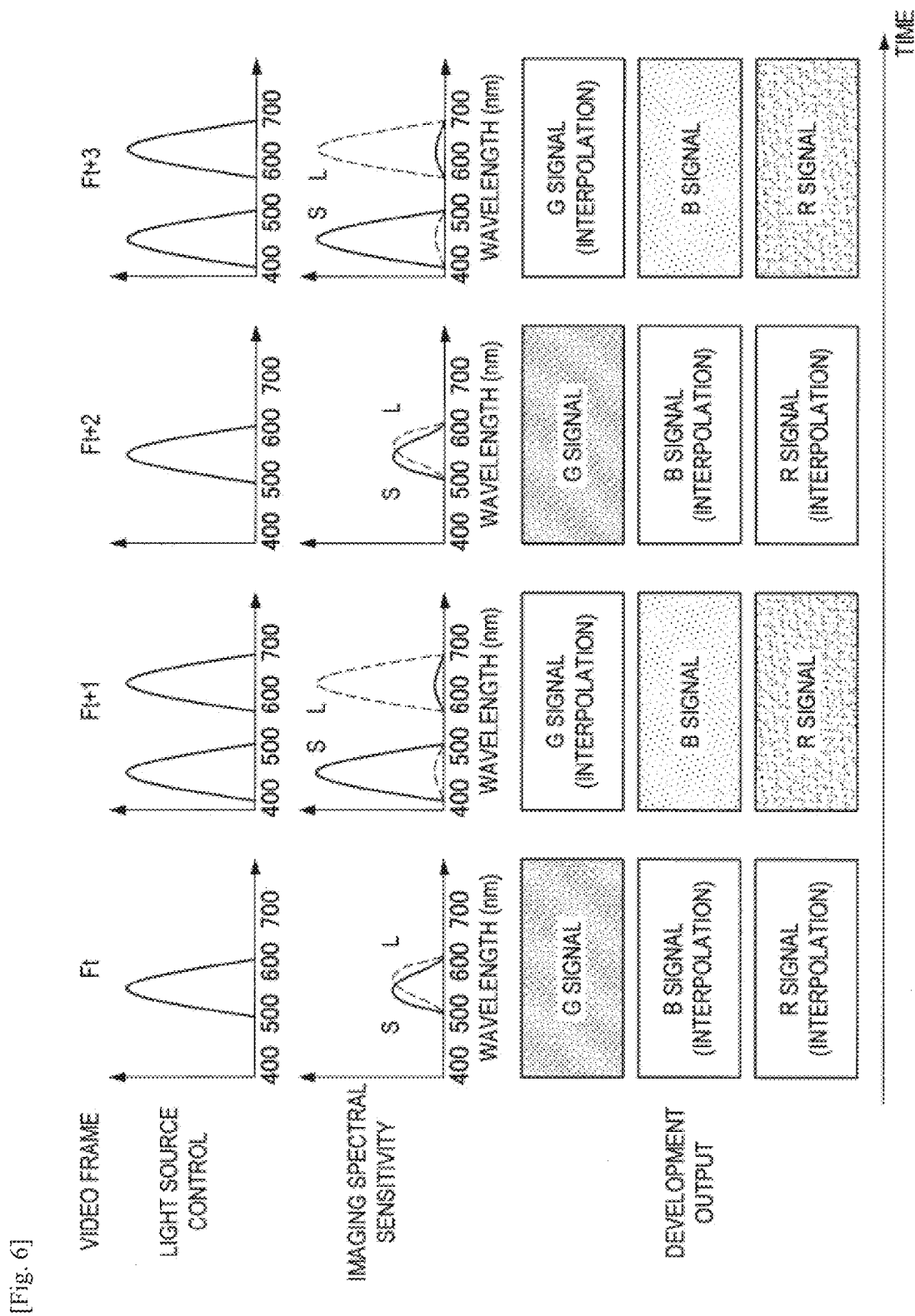
[Fig. 6]

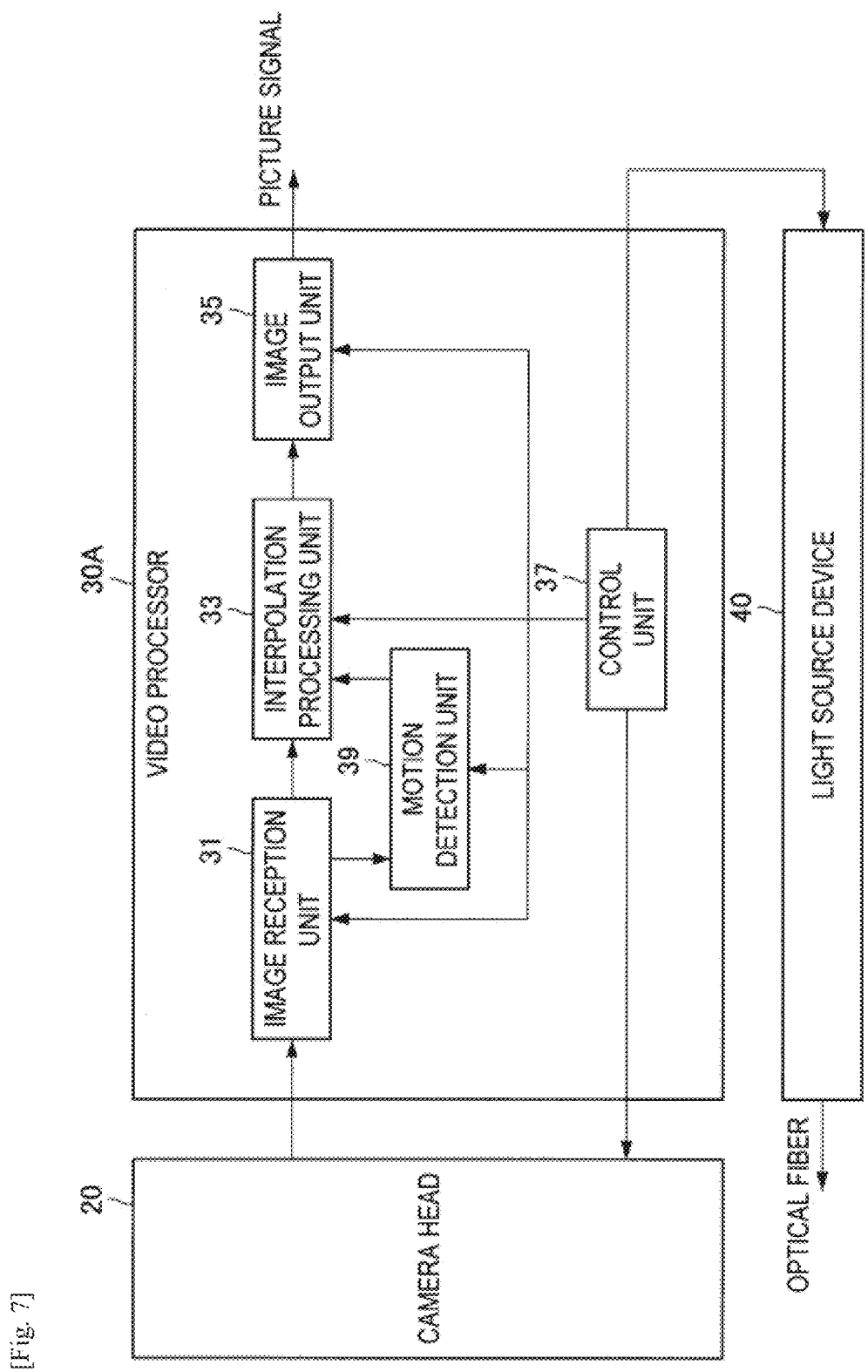

[Fig. 8]
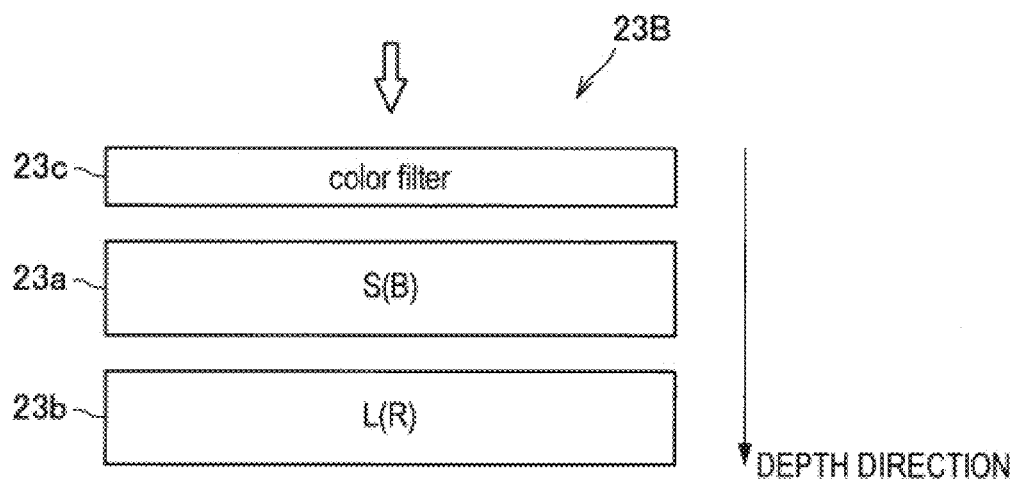
[Fig. 9]
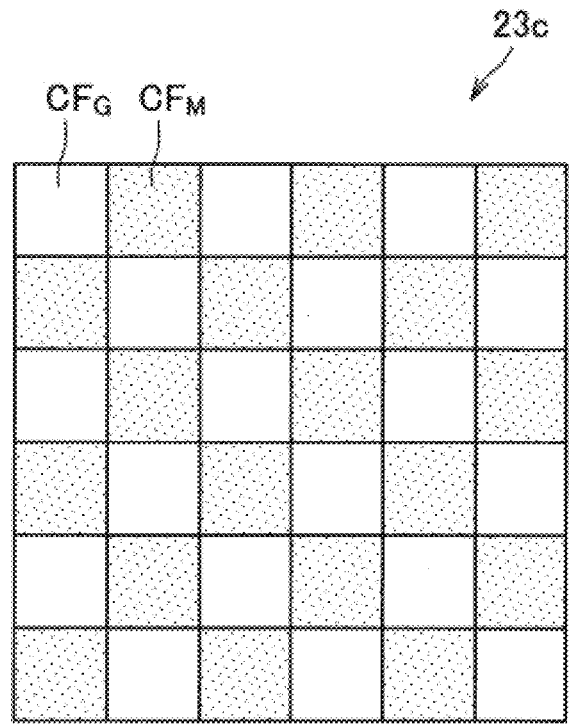

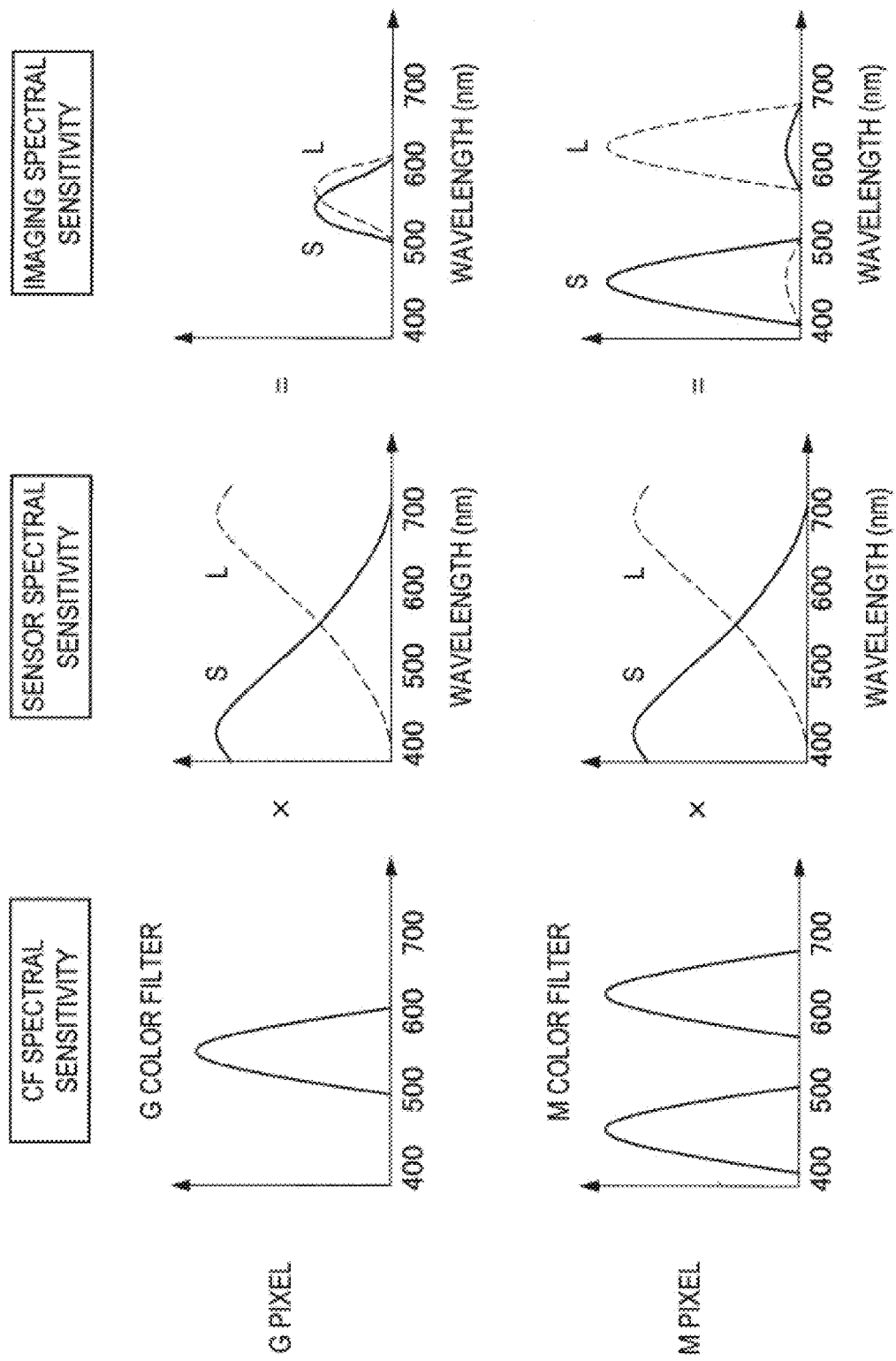
[Fig. 10]

[Fig. 11]
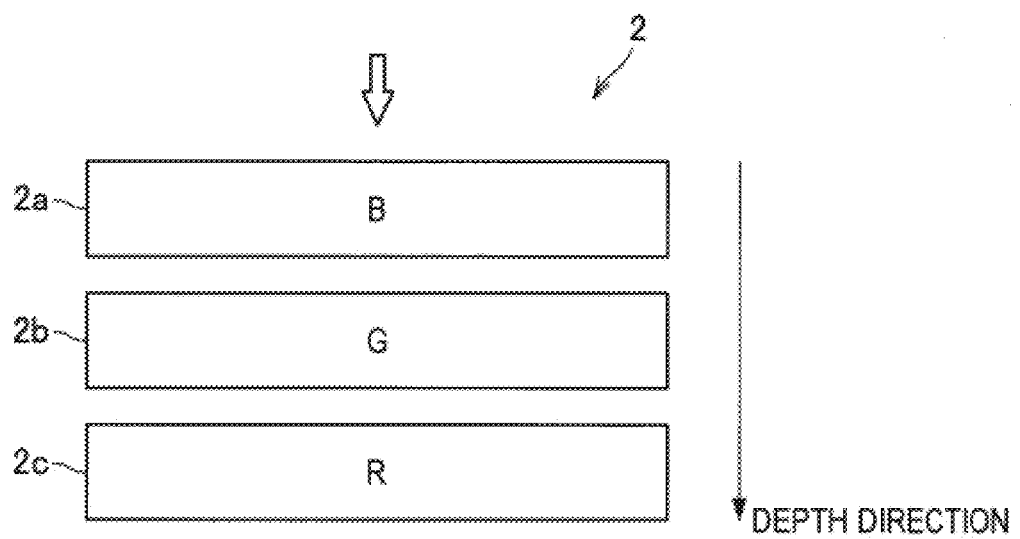

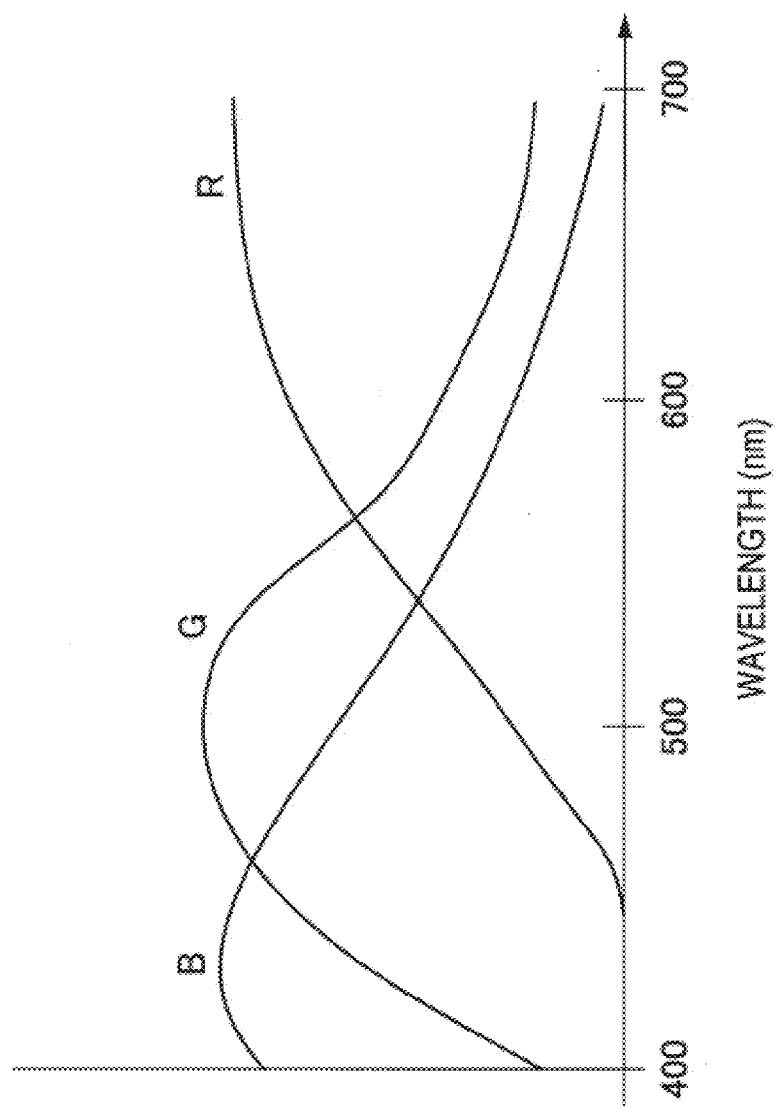
[Fig. 12]

ated in the technical field of the present disclosure from the description of the present specification may be achieved.

MEDICAL IMAGING APPARATUS, IMAGING METHOD, AND IMAGING APPARATUS

CROSS REFERENCE TO RELATED APPLICATIONS

This application is a U.S. National Phase of International Patent Application No. PCT/JP2016/001904 filed on Apr. 5, 2016, which claims priority benefit of Japanese Patent Application No. JP 2015-097020 filed in the Japan Patent Office on May 12, 2015. Each of the above-referenced applications is hereby incorporated herein by reference in its entirety.

TECHNICAL FIELD

The present disclosure relates to a medical imaging apparatus, an imaging method, and an imaging apparatus.

BACKGROUND ART

There has been proposed in related art an image sensor (solid-state image sensor) that photoelectrically converts light with different wavelengths by using photodiodes formed at different depths in a silicon substrate (e.g., PTL 1). In such an image sensor, as illustrated in FIG. 11, a pixel 2 includes photodiodes (photoelectric conversion units) of three layers 2a, 2b, and 2c for acquiring light of wavelength bands corresponding to the respective colors, blue (B), green (G), and red (R). However, as shown by the spectral sensitivity curve in FIG. 12, wavelength separation properties obtained by forming the photodiodes at different depths in the silicon substrate are not high. In the wavelength bands absorbed by the sensors in the layers of the respective colors, blue (B), green (G), and red (R), illustrated in FIG. 12, wavelengths absorbed by sensors in the other layers are also mixed much. This is called color mixing, which has been found to influence the color reproducibility of an image sensor and cause image quality degradation.

To solve the above problem of image quality degradation, there has been proposed an image sensor having a structure in which an organic photoelectric conversion layer and an inorganic photoelectric conversion layer made of silicon are stacked (e.g., PTL 2). Such an image sensor extracts at least a signal of light of a wavelength band corresponding to green (G) in the organic photoelectric conversion layer, and extracts signals of light of wavelength bands corresponding to red (R) and blue (B) in the inorganic photoelectric conversion layer. In this structure, the organic photoelectric conversion layer corresponding to a G pixel provided on the light-receiving surface side absorbs light of a wavelength band centered on green (G); thus, wavelength separation of red (R) and blue (B) in the inorganic photoelectric conversion layer is improved and the problem of color mixing is less likely to occur.

CITATION LIST

Patent Literature

[PTL 1]
JP 2002-513145T
[PTL 2]
JP 2008-258474A
[PTL 3]
JP 2013-220254A

SUMMARY

Technical Problem

An endoscope apparatus for surgery, such as laparoscopic surgery and thoracoscopic surgery, is used with a rigid scope including optical lenses being attached to a camera head equipped with a CCD or CMOS image sensor. In such an endoscope apparatus, sterilization is necessary for multiple times of use, and high-pressure steam sterilization using an autoclave is usually performed. Being placed in high-temperature environment of approximately 130° C. during high-pressure steam sterilization, the camera head and the rigid scope of the endoscope apparatus are desired to have heat resistance. However, an organic material like the organic photoelectric conversion layer in PTL 2 is generally easily affected by heat and thus is unsuitable for an image sensor of equipment that needs to be subjected to high-pressure steam sterilization.

Hence, the present disclosure proposes a novel and improved medical imaging apparatus, imaging method, and imaging apparatus including an image sensor with heat resistance.

Solution to Problem

According to an embodiment of the present disclosure, there is provided a medical imaging apparatus including a solid-state image sensor that includes a photoelectric converter having at least two photoelectric conversion layers stacked with respect to a light-receiving surface and separating received light into light of different wavelength bands, and circuitry configured to control a light source device that illuminates a subject.

According to an embodiment of the present disclosure, there is provided an imaging method including imaging a photographic subject using a solid-state image sensor that includes a photoelectric converter having at least two photoelectric conversion layers stacked with respect to a light-receiving surface and separating received light into light of different wavelength bands, and controlling, using circuitry, light emission of a light source device to illuminate the photographic subject with light of a predetermined wavelength band.

Furthermore, according to an embodiment of the present disclosure, there is provided A medical imaging system including an imaging apparatus configured to obtain images of a subject, the imaging apparatus including: a solid-state image sensor that includes a photoelectric converter having at least two photoelectric conversion layers stacked with respect to a light-receiving surface and separating received light into light of different wavelength bands, and circuitry configured to control a light source device that illuminates the subject and image processing circuitry configured to perform image signal processing on the images of the subject obtained by the imaging apparatus.

Advantageous Effects of Invention

As described above, according to an embodiment of the present disclosure, a medical imaging apparatus, imaging method, and imaging apparatus including an image sensor with heat resistance can be implemented. Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1 is an explanatory diagram illustrating a schematic configuration of an endoscope apparatus system according to a first embodiment of the present disclosure.

FIG. 2 is a block diagram illustrating configurations of a camera head, a video processor, and a light source device that are included in the endoscope apparatus system according to the embodiment.

FIG. 3 is an explanatory diagram for describing a configuration of an image sensor of the camera head according to the embodiment.

FIG. 4 is an explanatory diagram illustrating spectral sensitivity characteristics of the image sensor of FIG. 3.

FIG. 5 is an explanatory diagram illustrating imaging spectral characteristics in the endoscope apparatus system according to the embodiment.

FIG. 6 is an explanatory diagram illustrating the flow until image output in the endoscope apparatus system according to the embodiment.

FIG. 7 is a block diagram illustrating another example configuration of a video processor according to the embodiment.

FIG. 8 is an explanatory diagram illustrating a configuration of an image sensor of a camera head according to a second embodiment of the present disclosure.

FIG. 9 is a schematic plan view of an example configuration of a color filter of the image sensor illustrated in FIG. 8.

FIG. 10 is an explanatory diagram illustrating imaging spectral characteristics in an endoscope apparatus system according to the embodiment.

FIG. 11 is an explanatory diagram illustrating an example structure of an image sensor according to a related technology of the present disclosure.

FIG. 12 is an explanatory diagram illustrating an example of a spectral sensitivity curve of the image sensor of FIG. 11.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Description is given in the following order.
1. First embodiment (synchronization between imaging timing and light source emission)
 1.1. Configuration of endoscope apparatus system
 1.2. Photographing by endoscope apparatus system
 1.3. Conclusion
2. Second embodiment (color filter)
 2.1. Configuration of image sensor
 2.2. Imaging method
 2.3. Conclusion
3. Modification example
 3.1. Concerning detected wavelength band
 3.2. Application target 1. First Embodiment (1.1. Configuration of Endoscope Apparatus System)

First, a schematic configuration of an endoscope apparatus system 1 according to a first embodiment of the present disclosure will be described referring to FIGS. 1 and 2. FIG. 1 is an explanatory diagram illustrating a schematic configuration of the endoscope apparatus system 1 according to the present embodiment. FIG. 2 is a block diagram illustrating configurations of a camera head 20, a video processor 30, and a light source device 40 that are included in the endoscope apparatus system 1 according to the present embodiment.

The endoscope apparatus system 1 according to the present embodiment is, as illustrated in FIG. 1, a medical imaging apparatus including a rigid scope 10, the camera head 20, the video processor 30, the light source device 40, and a monitor 50. Note that in the present disclosure, a medical imaging apparatus refers to an imaging apparatus including at least an image sensor of the camera head 20.

The rigid scope 10 is an endoscope whose insertion portion, which is inserted into a patient's body, is made of a rigid material, and includes a plurality of optical lenses. The rigid scope 10 is connected to the light source device 40 by an optical fiber 65, and light from the light source device 40 is emitted from the insertion portion via the optical fiber 65 to illuminate an observation target, which is a photographic subject. The camera head 20 is connected to the other end (the side opposite to the insertion portion) of the rigid scope 10.

The camera head 20 images the observation target via the rigid scope 10. The camera head 20 is connected to the rigid scope 10 by a coupler (not illustrated). The camera head 20 includes, as illustrated in FIG. 2, an imaging lens 21 that forms an image of the observation target on an image sensor 23 via the rigid scope 10, the image sensor 23 that acquires the image of the observation target, and an image transmission unit 25 that sends and receives data to/from the image sensor 23.

The image formed by the imaging lens 21 is electronized in the image sensor 23, and transmitted, as raw image format (RAW) image data, from the image transmission unit 25 to the video processor 30 via an image transmission cable 61. In addition, the image transmission unit 25 receives an instruction from the video processor 30 via the image transmission cable 61, and outputs a control signal to the image sensor 23. The camera head 20 according to the present embodiment, which is a member to be subjected to high-pressure steam sterilization using an autoclave, is desired to have heat resistance.

The video processor 30 performs interpolation processing and the like on the image captured in the camera head 20, and develops the image. The video processor 30 includes, as illustrated in FIG. 2, an image reception unit 31, an interpolation processing unit 33, an image output unit 35, and a control unit 37.

When receiving the RAW image data from the camera head 20 in the image reception unit 31, the video processor 30 executes camera signal processing in the interpolation processing unit 33 to convert the RAW image data to image data signals displayable on a monitor. The image data having been converted in the interpolation processing unit 33 is output, via the image output unit 35, to the external monitor 50 connected to the video processor 30 by a video cable 67. The control unit 37 controls each processing unit of the video processor 30 in accordance with a picture synchronizing pulse, and outputs a control signal to the camera head 20 to control the camera head 20. In addition, the control unit 37 outputs a control signal to the light source device 40 via a control line 63 to cause light to illuminate the observation target to be emitted in conjunction with image processing.

The light source device 40 supplies illumination to the rigid scope 10. The light source device 40 includes a light source control unit 41, a light emission unit 43, and a light output unit 45. The light source control unit 41 controls light emission of the light emission unit 43, on the basis of the control signal from the video processor 30. The light emission unit 43 is a light source capable of emitting light of a visible light region. In the present embodiment, the light emission unit 43 is configured to be able to emit light of blue (B), green (G), and red (R). Light emitted from the light emission unit 43 is output from the light output unit 45 to the rigid scope 10 via the optical fiber 65. The light source device 40 according to the present embodiment is configured to be able to control a light emission pattern of the light emission unit 43 in accordance with an imaging frame rate of the image sensor 23. Hence, the light emission unit 43 is configured with a device capable of high-speed light emission control, such as an LED and a laser device.

The monitor 50 is an output device that displays the image generated by the video processor 30. The monitor 50 may be, for example, a liquid crystal display device or an organic EL display device.

The configuration of the endoscope apparatus system 1 according to the present embodiment has been described above.

(1.2. Photographing by Endoscope Apparatus System)

Next, a method for imaging an observation target by the endoscope apparatus system 1 according to the present embodiment will be described referring to FIGS. 3 to 7.

(1) Configuration of Image Sensor

In describing the method for imaging an observation target by the endoscope apparatus system 1 according to the present embodiment, first, a configuration of the image sensor 23 of the camera head 20 according to the present embodiment will be described on the basis of FIGS. 3 and 4. FIG. 3 is an explanatory diagram for describing the configuration of the image sensor 23 of the camera head 20 according to the present embodiment. FIG. 4 is an explanatory diagram illustrating spectral sensitivity characteristics of the image sensor 23 of FIG. 3.

The camera head 20 of the endoscope apparatus system 1 according to the present embodiment includes the image sensor 23 disposed, for example, on the distal end on the endoscope and that includes a photoelectric conversion unit in which two or more photoelectric conversion layers are stacked in a silicon substrate in the depth direction from a light-receiving surface, and is capable of separating light of different wavelength bands. For example, as illustrated in FIG. 3, a photoelectric conversion unit 23A includes, in the depth direction from the light-receiving surface, two photoelectric conversion layers 23a and 23b for acquiring light of different wavelength bands. The first photoelectric conversion layer 23a on the light-receiving surface side is a pixel that absorbs short wavelengths and performs photoelectric conversion (hereinafter also called "S pixel"). The second photoelectric conversion layer 23b below the first photoelectric conversion layer 23a is a pixel that absorbs long wavelengths and performs photoelectric conversion (hereinafter also called "L pixel"). For example, the S pixel is a blue pixel (B pixel), and the L pixel is a red pixel (R pixel). The image sensor 23 including such a photoelectric conversion unit does not include an organic photoelectric conversion layer and thus can be subjected to high-pressure steam sterilization.

In a stacked solid-state image sensor like the image sensor 23 according to the present embodiment, lowering of resolution can be suppressed. For comparison, in a single-chip solid-state image sensor, for example, a reduction in pixel size causes image quality degradation due to lowered sensitivity and lowered resolution attributed to a color filter array. In contrast, in a stacked solid-state image sensor, one pixel can acquire signals of a plurality of wavelength ranges; thus, lowering of resolution can be suppressed. In addition, light to be absorbed by a color filter can be acquired without being lost; thus, lowering of sensitivity can also be suppressed.

On the other hand, in a stacked solid-state image sensor, it has been found that color mixing occurs because the wavelength separation properties are not high, as described above, and results in image quality degradation. In view of this, as in PTL 2, for example, stacking organic photoelectric conversion layers to make color mixing less likely to occur has been proposed; however, this is not applicable to the endoscope apparatus system 1 according to the present embodiment because an organic material does not have heat resistance enough to withstand high-pressure steam sterilization.

Hence, the image sensor 23 according to the present embodiment has a configuration in which an organic photoelectric conversion layer is not placed and light of wavelength bands corresponding to blue (B) and red (R) is acquired in the inorganic photoelectric conversion layers 23a and 23b. In addition, light emission of the light source device 40 is controlled in synchronization with the imaging timing by the image sensor 23; thus, G signals and R and B signals are separated in time division.

That is, as illustrated in FIG. 3, in the image sensor 23 in which the first photoelectric conversion layer 23a functioning as a blue pixel (B pixel) and the second photoelectric conversion layer 23b functioning as a red pixel (R pixel) are stacked, wavelength separation properties corresponding to the depth of the silicon substrate are not so high. For example, as illustrated in FIG. 4, there is a portion where wavelength bands of absorbed light of the B pixel and the R pixel overlap with each other. Therefore, light of a wavelength band of green (G) between blue (B) and red (R) is photoelectrically converted in both the first photoelectric conversion layer 23a as the B pixel and the second photoelectric conversion layer 23b as the R pixel. Hence, in the present embodiment, to prevent color mixing, the wavelength band of light emitted by the light source device 40 is changed in time division so as to separate light of wavelength bands corresponding to the respective colors; thus, image quality degradation is prevented.

(2) Imaging Method

Hereinafter, the method for imaging an observation target in the endoscope apparatus system 1 according to the present embodiment will be described in detail on the basis of FIGS. 5 to 7. FIG. 5 is an explanatory diagram illustrating imaging spectral characteristics in the endoscope apparatus system 1 according to the present embodiment. FIG. 6 is an explanatory diagram illustrating the flow until image output in the endoscope apparatus system 1 according to the present embodiment. FIG. 7 is a block diagram illustrating another example configuration of a video processor according to the present embodiment.

In the endoscope apparatus system 1 according to the present embodiment, the image sensor 23 and the light source device 40 work together and, in time series, the light source device 40 emits light of different wavelength bands and the image sensor 23 acquires signals of green (G) and signals of red (R) and blue (B). FIG. 5 shows a conceptual diagram illustrating imaging spectral characteristics.

The light source device 40 emits light of a predetermined wavelength band in accordance with the imaging timing of the image sensor 23, on the basis of a vertical synchronization signal given from the control unit 37 of the video processor 30. For example, as illustrated in FIG. 5, at a certain time t, the light source control unit 41 of the light source device 40 causes the light emission unit 43 to emit light of a wavelength band of green (G), which is shown on the left in the upper stage of FIG. 5, in accordance with the imaging timing of the image sensor 23. At this time, the S pixel (blue pixel here) and the L pixel (red pixel here) of the image sensor 23 absorb light with sensor spectral sensitivity characteristics shown in the middle in the upper stage of FIG. 5. Thus, imaging is performed by the S pixel and the L pixel with imaging spectral sensitivity characteristics as shown on the right in the upper stage of FIG. 5.

Signals of the S pixel and the L pixel of the image sensor 23 are output from the image transmission unit 25 to the video processor 30. Then, in the interpolation processing unit 33, the S pixel signal and the L pixel signal shown on the right in the upper stage of FIG. 5 are summed and a pixel signal of green (G) is obtained.

Then, the light source device 40 emits light of magenta (M) in response to an instruction from the control unit 37 at a time t+1 following the time t. The light of magenta (M) is emitted by mixing red light emission and blue light emission. The light source control unit 41 of the light source device 40 causes the light emission unit 43 to emit light of wavelength bands of blue (B) and red (R) so as to emit light of magenta (M), as shown on the left in the lower stage of FIG. 5, in accordance with the imaging timing of the image sensor 23. At this time, the S pixel (blue pixel here) and the L pixel (red pixel here) of the image sensor 23 absorb light with sensor spectral sensitivity characteristics shown in the middle in the lower stage of FIG. 5. Thus, imaging is performed by the S pixel and the L pixel with imaging spectral sensitivity characteristics as shown on the right in the lower stage of FIG. 5.

Signals of the S pixel and the L pixel of the image sensor 23 are output from the image transmission unit 25 to the video processor 30. Then, in the interpolation processing unit 33, the S pixel signal shown on the right in the lower stage of FIG. 5 is obtained as a pixel signal of blue (B). In addition, the L pixel signal shown on the right in the lower stage of FIG. 5 is obtained as a pixel signal of red (R).

The control unit 37 of the video processor 30 repeats the above-described imaging operation of the time t and the time t+1. Thus, a frame (G frame) in which G pixels are acquired in all the pixels included in the image sensor 23 and a frame (RB frame) in which B pixels and R pixels are acquired simultaneously in all the pixels included in the image sensor 23 are implemented alternately. The interpolation processing unit 33 of the video processor 30 performs synchronization processing from signals of the G frame and the RB frame; thus, image data having a blue (B) pixel, a green (G) pixel, and a red (R) pixel can be output for all the pixels of the image sensor 23.

FIG. 6 illustrates the flow until image output in the endoscope apparatus system 1 according to the present embodiment. The horizontal direction of FIG. 6 represents time, which shifts to the right side row by row in synchronization with video frames. The camera head 20, the video processor 30, and the light source device 40 are synchronized by a video synchronization signal.

First, in a frame Ft, light of green (G) is emitted in the light source device 40. As described above, the imaging spectral characteristics are as shown in the second stage from the top of FIG. 6, owing to the combination of light source spectral intensity and spectral sensitivity characteristics of the image sensor 23. At this time, the interpolation processing unit 33 of the video processor 30 adds up the luminance values of the S pixels and the L pixels output from the image sensor 23 to generate the luminance values of green (G) pixels in the entire image sensor 23.

Next, in a frame Ft+1, light of magenta (M) is emitted in the light source device 40. As described above, the imaging spectral characteristics are as shown in the second stage from the top of FIG. 6, owing to the combination of light source spectral intensity and spectral sensitivity characteristics of the image sensor 23. Note that the luminance value of the S pixel of the image sensor is that of a blue (B) pixel, and the luminance value of the L pixel is that of a red (R) pixel. Thus, the interpolation processing unit 33 of the video processor 30 generates the luminance values of blue (B) pixels and red (R) pixels in the entire image sensor 23.

Here, the luminance values of blue (B) pixels and red (R) pixels in the frame Ft may be generated by interpolation processing from earlier and later frames. As the interpolation processing, for example, zero-order interpolation processing may be applied in which the luminance values of blue (B) pixels and the luminance values of red (R) pixels in a frame Ft−1, which is one frame before the frame Ft, are used without change. Alternatively, first-order interpolation processing may be applied in which linear interpolation is performed from the luminance values of blue (B) pixels and the luminance values of red (R) pixels in the frame Ft−1, which is one frame before the frame Ft, and the luminance values of blue (B) pixels and the luminance values of red (R) pixels in a frame Ft+1, which is one frame after the frame Ft.

Furthermore, the interpolation processing unit 33 may perform interpolation processing in accordance with a motion of an object in images detected between earlier and later frames. In this case, as illustrated in FIG. 7, for example, a video processor 30A may be provided with a motion detection unit 39. The motion detection unit 39 is controlled by the control unit 37 in accordance with a picture synchronizing pulse. When receiving the RAW image data that the image reception unit 31 has received, the motion detection unit 39 detects a motion of an object in images, and outputs the detected motion to the interpolation processing unit 33 as motion information. Thus, the interpolation processing unit 33 can perform motion compensation of the image data input from the image reception unit 31, on the basis of the motion information received from the motion detection unit 39.

The interpolation processing unit 33 performs such interpolation processing to generate the luminance values of blue (B) pixels and red (R) pixels in the entire image sensor 23 in the frame Ft.

Similarly, the luminance values of green (G) pixels in the frame Ft+1 may be subjected to interpolation processing using the luminance values of green (G) pixels in the frame Ft, which is one frame before the frame Ft+1, and the luminance values of green (G) pixels in a frame Ft+2, which is one frame after the frame Ft+1. Thus, the luminance values of green (G) pixels in the entire image sensor 23 are generated.

Such interpolation processing may use a technology as described in PTL 3, for example. The interpolation processing unit 33 further performs color correction processing, such as white balance processing by gain adjustment of R, G, and B, and image quality improvement processing, such as noise reduction processing, to generate final picture signals.

In the above processing, the generation of the luminance values of green (G) pixels and the generation of the luminance values of blue (B) pixels and red (R) pixels are performed repeatedly as the video frame proceeds to frames Ft+2, Ft+3, and so on. That is, in the endoscope apparatus system 1 according to the present embodiment, imaging is performed in time division through a frame in which image signals of green (G) are acquired and a frame in which image signals of blue (B) and image signals of red (R) are acquired.

Note that when an imaging frame rate is set to twice a picture output frame rate, one picture output frame rate can include two imaging frame rates of the G frame and the RB frame. That is, all signals of blue (B), green (G), and red (R) can be acquired for each frame in the picture output frame rate. Such double-speed imaging allows images with higher resolution to be obtained.

(1.3. Conclusion)

The configuration of the endoscope apparatus system 1 according to the first embodiment of the present disclosure and the method for imaging an observation target by the endoscope apparatus system 1 have been described above. According to the present embodiment, by using the stacked image sensor 23, in comparison with a single-chip image sensor having color filters arranged and performing color division, the red (R), green (G), and blue (B) luminance values can be obtained in all the pixels. Thus, the resolution of the obtained image can be increased.

In medical equipment such as an endoscope apparatus for surgery, like the endoscope apparatus system 1 according to the present embodiment, high-pressure steam sterilization is performed in some cases; hence, the image sensor 23 is desired to have heat resistance. The endoscope apparatus system 1 according to the present embodiment can be implemented without using an organic material for the image sensor 23 and thus has heat resistance enough to withstand high-pressure steam sterilization.

In addition, in the endoscope apparatus system 1 according to the present embodiment, the luminance values of red (R), green (G), and blue (B) pixels can be obtained by time division processing of two frames. In imaging in time division in related art using a light source device that emits light of red (R), green (G), and blue (B) and a single-chip monochrome image sensor, the red (R), green (G), and blue (B) luminance values can be obtained, but large time lags cause color breakup (so-called color breaking). The imaging method according to the present embodiment can be reduce the occurrence of color breakup because the luminance values of red (R), green (G), and blue (B) pixels can be obtained by time division processing of two frames.

Furthermore, the endoscope apparatus system 1 according to the present embodiment achieves color separation in wavelength bands where color mixing occurs, by controlling light emission of the light source device 40 in synchronization with the imaging timing of the image sensor 23. This can prevent color mixing that occurs in a stacked image sensor in related art and prevent image quality degradation.

According to another embodiment, the light source device 40 which is controlled in synchronization with the imaging timing of the image sensor 23 is controlled to reduce the light of a blue wavelength band and the light of a red light wavelength band at a first timing and the light of a green wavelength band at a second timing.

2. Second Embodiment

Next, an endoscope apparatus system according to a second embodiment of the present disclosure will be described referring to FIGS. 8 to 10. The endoscope apparatus system according to the present embodiment differs from that of the first embodiment in the configuration of an image sensor, which eliminates the need for light emission control of the light source device 40. Hereinafter, differences from the first embodiment will be mainly described and detailed description of the same function and structure will be omitted.

(2.1. Configuration of Image Sensor)

First, a configuration of an image sensor of the endoscope apparatus system according to the present embodiment will be described referring to FIGS. 8 and 9. FIG. 8 is an explanatory diagram illustrating a configuration of an image sensor of a camera head according to the present embodiment. FIG. 9 is a schematic plan view of an example configuration of a color filter 23c of the image sensor illustrated in FIG. 8. Note that since the endoscope apparatus system itself has substantially the same configuration as the endoscope apparatus system 1 of the first embodiment illustrated in FIGS. 1 to 3, detailed description thereof is omitted here.

The image sensor provided in the camera head of the endoscope apparatus system according to the present embodiment includes a photoelectric conversion unit in which two or more photoelectric conversion layers are stacked in a silicon substrate in the depth direction from a light-receiving surface and is capable of separating light of different wavelength bands, and includes a color filter on the upper surface of the photoelectric conversion unit. For example, as illustrated in FIG. 8, a photoelectric conversion unit 23B includes, in the depth direction from the light-receiving surface, the two photoelectric conversion layers 23a and 23b for acquiring light of different wavelength bands and the color filter 23c provided above them.

The first photoelectric conversion layer 23a on the light-receiving surface side is a pixel that absorbs short wavelengths and performs photoelectric conversion (S pixel), and the second photoelectric conversion layer 23b below the first photoelectric conversion layer 23a is a pixel that absorbs long wavelengths and performs photoelectric conversion (L pixel). For example, the S pixel is a blue pixel (B pixel), and the L pixel is a red pixel (R pixel).

The color filter 23c is provided above the first photoelectric conversion layer 23a. In the color filter 23c, as illustrated in FIG. 9, green color filters $CF_G$ for extracting image signals of green (G) and magenta color filters $CF_M$ for extracting image signals of magenta (M), that is, image signals of blue (B) and red (R), are arranged in a checkered pattern. That is, the color filter 23c produces a state where green (G) pixels and magenta (M) pixels are arranged in space division. Note that in the case where the camera head 20 is subjected to high-pressure steam sterilization, the color filter 23c is formed using an inorganic material in order to increase heat resistance. In the case where the image sensor 23 is not provided in equipment that is desired to have heat resistance, like an endoscope apparatus system, the color filter 23c may be formed using an organic material.

The image sensor 23 according to the present embodiment can separate light of wavelength bands corresponding to the respective colors alone; hence, there is no need to synchronize a light source device of the endoscope apparatus system with the imaging timing of the image sensor 23. The light source device may be any device that is capable of producing white light, for example, and only needs to illuminate an observation target with light during photographing by the image sensor 23.

(2.2. Imaging Method)

Hereinafter, a method for imaging an observation target in the endoscope apparatus system according to the present embodiment will be described in detail on the basis of FIG. 10. FIG. 10 is an explanatory diagram illustrating imaging spectral characteristics in the endoscope apparatus system according to the present embodiment.

In the endoscope apparatus system according to the present embodiment, the image sensor 23 including the color filter 23c acquires signals of light of different wavelength bands in space division. That is, in a region provided with the green color filter $CF_G$, the wavelength band of light to be absorbed by the S pixel and the L pixel is the wavelength band of green (G), as shown on the left in the upper stage of FIG. 10. The light that has passed through the green color filter $CF_G$ is absorbed by the S pixel and the L pixel with sensor spectral sensitivity characteristics shown in the middle in the upper stage of FIG. 10. Thus, imaging is performed by the S pixel and the L pixel with imaging spectral sensitivity characteristics as shown on the right in the upper stage of FIG. 10.

Signals of the S pixel and the L pixel of the image sensor 23 are output from the image transmission unit 25 to the video processor 30. Then, in the interpolation processing unit 33, the S pixel signal and the L pixel signal shown on the right in the upper stage of FIG. 10 are summed and a pixel signal of green (G) is obtained.

In a region provided with the magenta color filter $CF_M$, the wavelength bands of light to be absorbed by the S pixel and the L pixel are the wavelength bands of magenta (M), that is, blue (B) and red (R), as shown on the left in the lower stage of FIG. 10. The light that has passed through the magenta color filter $CF_M$ is absorbed by the S pixel and the L pixel with sensor spectral sensitivity characteristics shown in the middle in the lower stage of FIG. 10. Thus, imaging is performed by the S pixel and the L pixel with imaging spectral sensitivity characteristics as shown on the right in the lower stage of FIG. 10.

Signals of the S pixel and the L pixel of the image sensor 23 are output from the image transmission unit 25 to the video processor 30. Then, in the interpolation processing unit 33, the S pixel signal shown on the right in the lower stage of FIG. 10 is obtained as a pixel signal of blue (B). In addition, the L pixel signal shown on the right in the lower stage of FIG. 10 is obtained as a pixel signal of red (R).

As described above, by using the image sensor 23 of the endoscope apparatus system according to the present embodiment, image signals of the respective pixels can be acquired in space division in each imaging frame.

(2.3. Conclusion)

The configuration of the image sensor of the endoscope apparatus system according to the second embodiment of the present disclosure and the method for imaging an observation target by the image sensor have been described above. According to the present embodiment, the stacked image sensor 23 including a color filter is used. The image sensor 23 configured without using an organic material can have heat resistance enough to withstand high-pressure steam sterilization. In addition, since the image sensor 23 according to the present embodiment photographs an observation target in space division by using the color filter, there is no need to synchronize light emission control of the light source device with the imaging timing of the image sensor 23 and a system with high versatility can be implemented.

3. Modification Example (3.1. Concerning Detected Wavelength Band)

The image sensor 23 according to the first embodiment is configured to be able to separate wavelength bands of blue (B) and red (R), and the image sensor 23 according to the second embodiment is configured to be able to separate wavelength bands of blue (B), green (G), and red (R) by using the color filter 23c. The present disclosure, however, is not limited to such examples. It is also possible to separate wavelength bands other than the wavelength bands of blue (B), green (G), and red (R) by applying the system configuration of the above first embodiment or second embodiment.

For example, by applying the system configuration of the above embodiment, it is possible to separate wavelength bands of infrared (IR) as well as blue (B), green (G), and red (R). In the case where the image sensor 23 and the light source device 40 work together to separate the wavelength bands as in the first embodiment, emission of light of the wavelength bands of green (G) and infrared (IR) and emission of light of the wavelength bands of blue (B) and red (R) may be performed alternately.

It is also possible to separate, by applying the system configuration of the above embodiment, light (special light) including two narrow-band wavelengths as in narrow band imaging (NBI). In NBI, an observation target is illuminated with narrow-band light, such as blue light of 390 to 445 nm and green light of 530 to 550 nm, and an image sensor acquires an image. Even in such a case, it is possible to separate light of individual wavelength bands by applying the system configuration of the first embodiment or the second embodiment.

(3.2. Application Target)

Although examples of the application to an endoscope apparatus system have been described in the above embodiments, without being limited to such examples, the present disclosure can be applied to equipment other than medical equipment such as an endoscope apparatus system, and can be used as a versatile imaging apparatus.

For example, in the case where the image sensor 23 and the light source device 40 work together to separate the wavelength bands as in the first embodiment, the present disclosure can be applied to environment where light emission of the light source device 40 is controllable. Examples of such application include application to studio photography and the like where light from substantially only the light source device 40 enters.

In the case where light of individual wavelength bands is separated by using the color filter 23c as in the second embodiment, when the image sensor 23 is not provided in equipment that is desired to have heat resistance, like an endoscope apparatus system, the color filter 23c may be formed using an organic material. In the system configuration according to the second embodiment, light to illuminate an observation target may be white light; hence, the present disclosure can be applied to various situations.

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

A medical imaging apparatus including:
a solid-state image sensor that includes a photoelectric converter having at least two photoelectric conversion layers stacked with respect to a light-receiving surface and separating received light into light of different wavelength bands; and circuitry configured to control a light source device that illuminates a subject.

(2)

The medical imaging apparatus according (1), wherein each photoelectric conversion layer consists of non-organic material.

(3)

The medical imaging apparatus according to (1)-(2), wherein the circuitry controls light emission of the light source device in synchronization with imaging timing of the solid-state image sensor.

(4)

The medical imaging apparatus according to (1)-(3), wherein the photoelectric converter includes a first photoelectric conversion layer detecting light corresponding to a first wavelength band and a second photoelectric conversion layer detecting light corresponding to a second wavelength band, and
wherein the circuitry is configured to control the light source device to output light corresponding to the first wavelength band and light corresponding to the second wavelength band at a first timing, and to control the light source device to output light corresponding to a third wavelength band at a second timing, in synchronization with the imaging timing of the solid-state image sensor.

(5)

The medical imaging apparatus according to (1)-(3), wherein the photoelectric converter includes a first photoelectric conversion layer detecting light corresponding to a first wavelength band and a second photoelectric conversion layer detecting light corresponding to a second wavelength band, and
wherein the circuitry is further configured to control the light source device to reduce a light corresponding to the first wavelength band and light corresponding to the second wavelength band at a first timing, and to control the light source device to reduce light corresponding to a third wavelength band at a second timing, in synchronization with the imaging timing of the solid-state image sensor.

(6)

The medical imaging apparatus according to (1)-(5), wherein the light source device includes a plurality of laser emitting devices emitting laser light corresponding to red, green and blue light.

(7)

The medical imaging apparatus according to (1)-(6), wherein the light source device includes a white light source and an optical filter that selectively removes light of a particular wavelength band.

(8)

The medical imaging apparatus according to (1)-(7), wherein the circuitry is further configured to alternatively obtain an image corresponding to green light and an image corresponding to blue and red light.

(9)

The medical imaging apparatus according to (1)-(8), wherein the circuitry further configured to
interpolate a luminance signal of a pixel of a color that is not acquired in each imaging frame of image data acquired by the solid-state image sensor by using a luminance signal of a pixel acquired in a different imaging frame.

(10)

The medical imaging apparatus according to (1)-(9), wherein the circuitry further configured to detect a motion in the image data, and perform motion compensation processing on the basis of motion information in the image data.

(11)

The medical imaging apparatus according to (1)-(10), wherein the circuitry further configured to
interpolate a luminance signal of a pixel that was acquired in each imaging frame of image data acquired by the solid-state image sensor by using a luminance signal of a pixel of a same color acquired in a different imaging frame.

(12)

The medical imaging apparatus according to (1)-(11), wherein an imaging frame rate of the solid-state image sensor is set to twice a picture output frame rate.

(13)

The medical imaging apparatus according to (1)-(12), wherein the solid-state image sensor outputs image data in a RAW image data format.

(14)

The medical imaging apparatus according to (1), wherein a color filter layer is provided on the photoelectric converter.

(15)

The medical imaging apparatus according to (14), wherein the photoelectric converter includes a first photoelectric conversion layer detecting light corresponding to a first wavelength band and a second photoelectric conversion layer detecting light corresponding to a second wavelength band, and
wherein the color filter layer includes a first color filter through which light corresponding to a third wavelength band passes and a second color filter through which light corresponding to the first wavelength band and the second wavelength band passes.

(16)

The medical imaging apparatus according to (1)-(15), wherein the medical imaging apparatus is autoclave compatible.

(17)

The medical imaging apparatus according to (1)-(16), wherein the medical imaging apparatus is an endoscope.

(18)

The medical imaging apparatus according to (17), wherein the endoscope further includes a light source.

(19)

The medical imaging apparatus according to (1)-(18), wherein the solid-state image sensor is disposed on the distal end of the endoscope.

(20)

The medical imaging apparatus according to (1)-(19), wherein at least one wavelength band on the different wavelength bands is an infrared wavelength band.

(21)

The medical imaging apparatus according to (1)-(20), wherein the solid-state image sensor outputs both a normal image in a visual wavelength band and an infrared image in the infrared wavelength band.

(22)

The medical imaging apparatus according to (1)-(21), wherein the first wavelength band is a blue wavelength band, the second wavelength band is a red wavelength band and the third wavelength band is a green wavelength band.

(23)

An imaging method including:

imaging a photographic subject using a solid-state image sensor that includes a photoelectric converter having at least two photoelectric conversion layers stacked with respect to a light-receiving surface and separating received light into light of different wavelength bands; and controlling, using circuitry, light emission of a light source device to illuminate the photographic subject with light of a predetermined wavelength band.

(24)

The imaging method according to (23), further including:

controlling, using the circuitry, the light emission of the light source device to illuminate the photographic subject with light of a predetermined wavelength band in synchronization with imaging timing of the solid-state image sensor.

(25)

A medical imaging system, including:

an imaging apparatus configured to obtain images of a subject, the imaging apparatus including:
  a solid-state image sensor that includes a photoelectric converter having at least two photoelectric conversion layers stacked with respect to a light-receiving surface and separating received light into light of different wavelength bands, and
  circuitry configured to control a light source device that illuminates the subject; and
image processing circuitry configured to perform image signal processing on the images of the subject obtained by the imaging apparatus.

(26)

A medical imaging apparatus including:

a solid-state image sensor that includes a photoelectric conversion unit in which at least two photoelectric conversion layers are stacked from a light-receiving surface and is capable of separating received light into light of different wavelength bands.

(27)

The medical imaging apparatus according to (26), further including:

a light source control unit configured to control a light source device that illuminates a photographic subject, wherein the light source control unit controls light emission of the light source device in synchronization with imaging timing of the solid-state image sensor.

(28)

The medical imaging apparatus according to (27), wherein the photoelectric conversion unit includes a first photoelectric conversion layer capable of detecting a blue wavelength band and a second photoelectric conversion layer capable of detecting a red wavelength band, and wherein the light source control unit causes the light source device to output light of a blue wavelength band and light of a red wavelength band at a first timing, and causes the light source device to output light of a green wavelength band at a second timing, in synchronization with the imaging timing of the solid-state image sensor.

(29)

The medical imaging apparatus according to (28), including:

an interpolation processing unit configured to perform interpolation processing on image data acquired by the solid-state image sensor, wherein the interpolation processing unit interpolates a luminance value of a pixel of a color that is not acquired in each imaging frame of the image data by using a luminance value of a pixel acquired in another imaging frame.

(30)

The medical imaging apparatus according to (29), including:

a motion detection unit configured to detect a motion of an object in the image data, wherein the interpolation processing unit performs motion compensation processing on the basis of motion information of the object in the image data input from the motion detection unit.

(31)

The medical imaging apparatus according to any one of (26) to (30), wherein an imaging frame rate of the solid-state image sensor is set to twice a picture output frame rate.

(32)

The medical imaging apparatus according to (26), wherein a color filter layer is provided on the photoelectric conversion unit.

(33)

The medical imaging apparatus according to (32), wherein the photoelectric conversion unit includes a first photoelectric conversion layer capable of detecting a blue wavelength band and a second photoelectric conversion layer capable of detecting a red wavelength band, and wherein the color filter layer includes a first color filter through which light of a green wavelength band passes and a second color filter through which light of a blue wavelength band and a red wavelength band passes.

(34)

The medical imaging apparatus according to any one of (26) to (33), wherein the medical imaging apparatus is capable of being subjected to high-pressure steam sterilization.

(35)

The medical imaging apparatus according to any one of (26) to (34), wherein the medical imaging apparatus is an endoscope.

(36)

An imaging method including:

imaging a photographic subject by using a solid-state image sensor that includes a photoelectric conversion unit in which at least two photoelectric conversion layers are stacked from a light-receiving surface and is capable of separating received light into light of different wavelength bands; and controlling light emission of a light source device by a light source control unit to illuminate the photographic subject with light of a predetermined wavelength band, in synchronization with imaging timing of the solid-state image sensor.

(37)

An imaging apparatus including:

a solid-state image sensor that includes a photoelectric conversion unit in which at least two photoelectric conversion layers are stacked from a light-receiving surface and is capable of separating received light into light of different wavelength bands.

REFERENCE SIGNS LIST 1 endoscope apparatus system
10 rigid scope
20 camera head
21 imaging lens
23 image sensor
23A, 23B photoelectric conversion unit
25 image transmission unit
30 video processor
31 image reception unit
33 interpolation processing unit
35 image output unit
37 control unit
39 motion detection unit
40 light source device
41 light source control unit
43 light emission unit
45 light output unit
50 monitor
61 image transmission cable
63 control line
65 optical fiber
67 video cable

The invention claimed is:

1. A medical imaging apparatus, comprising:
a solid-state image sensor configured to acquire a plurality of images, wherein
the solid-state image sensor includes a photoelectric converter configured to receive light on a light-receiving surface of the photoelectric converter,
the photoelectric converter includes at least two photoelectric conversion layers in a depth direction with respect to the light-receiving surface, and
the at least two photoelectric conversion layers is configured to separate the received light into light of different wavelength bands; and
circuitry configured to:
control light emission of a light source device that illuminates a subject, wherein the light emission of the light source device is controlled in synchronization with imaging timing of the solid-state image sensor; and
interpolate a first luminance signal associated with a first image frame, wherein
the first image frame corresponds to first image data,
the first image data associated with a first image of the plurality of images,
the first luminance signal is interpolated in synchronization with timing of the first image frame,
the first image is acquired in synchronization with the timing of the first image frame,
the first luminance signal is interpolated based on a second luminance signal associated with a second image frame,
the second image frame corresponds to second image data,
the second image data is associated with a second image of the plurality of images,
the second luminance signal is associated with the second image frame corresponds to a specific color, and
the first image frame is different from the second image frame.

2. The medical imaging apparatus according to claim 1, wherein each photoelectric conversion layer of the at least two photoelectric conversion layers comprises a non-organic material.

3. The medical imaging apparatus according to claim 1, wherein
the circuitry is further configured to alternatively obtain the first image and the second image, and
the first image corresponds to green light and the second image corresponds to blue light and red light.

4. The medical imaging apparatus according to claim 1, wherein
the circuitry is further configured to interpolate a third luminance signal associated with a third image frame, wherein
the third image frame corresponds to third image data,
the third image data is associated with a third image of the plurality of images,
the third luminance signal is interpolated based on a fourth luminance signal associated with a fourth image frame,
the fourth image frame corresponds to fourth image data,
the fourth image data is associated with a fourth image of the plurality of images,
the third luminance signal associated with the third image frame corresponds to the specific color, and
the specific color is not associated with each of the plurality of images.

5. The medical imaging apparatus according to claim 4, wherein the circuitry is further configured to:
detect a motion in each of the plurality of images; and
perform motion compensation process on each of the plurality of images based on the detected motion.

6. The medical imaging apparatus according to claim 1, wherein an image frame rate of each of the first image frame and the second image frame is twice a picture output frame rate.

7. The medical imaging apparatus according to claim 1, wherein the solid-state image sensor is further configured to output each of the first image data and the second image data in a RAW image data format.

* * * * *